US012569918B2

(12) United States Patent
Storz et al.

(10) Patent No.: US 12,569,918 B2
(45) Date of Patent: Mar. 10, 2026

(54) TOOL QUICK-CHANGE SET FOR MEDICAL HAND-HELD MACHINE TOOL

(71) Applicants: Olaf Storz, Tuttlingen (DE); Frederik Zepf, Tuttlingen (DE)

(72) Inventors: Olaf Storz, Tuttlingen (DE); Frederik Zepf, Tuttlingen (DE)

(73) Assignee: STUCKENBROCK MEDIZINTECHNIK GMBH, Tuttlingen (DE)

( * ) Notice: Subject to any disclaimer, the term of this patent is extended or adjusted under 35 U.S.C. 154(b) by 540 days.

(21) Appl. No.: 17/943,004

(22) Filed: Sep. 12, 2022

(65) Prior Publication Data

US 2023/0078274 A1      Mar. 16, 2023

(30) Foreign Application Priority Data

Sep. 10, 2021     (DE) ..................... 10 2021 123 551.0

(51) Int. Cl.
*B23B 31/113*          (2006.01)
*A61B 17/16*          (2006.01)
*A61B 17/00*          (2006.01)

(52) U.S. Cl.
CPC .......... *B23B 31/113* (2013.01); *A61B 17/162* (2013.01); *A61B 2017/00477* (2013.01)

(58) Field of Classification Search
CPC ............. B23B 31/10741; B23B 31/113; B23B 2240/04; B25G 3/16; A61B 17/162
See application file for complete search history.

(56) References Cited

U.S. PATENT DOCUMENTS

| | | | | |
|---|---|---|---|---|
| 1,886,177 A | * | 11/1932 | Gairing ................. | B23B 31/113 |
| | | | | 279/93 |
| 2,731,273 A | * | 1/1956 | Edens ................... | B23B 31/113 |
| | | | | 279/81 |
| 2,773,693 A | * | 12/1956 | Chittenden ........... | B23B 31/113 |
| | | | | 279/97 |
| 2,985,457 A | * | 5/1961 | Sima ..................... | B23B 31/113 |
| | | | | 279/93 |

(Continued)

FOREIGN PATENT DOCUMENTS

| | | |
|---|---|---|
| DE | 10357505 A1 | 5/2005 |
| DE | 102011113126 A1 | 3/2013 |

(Continued)

OTHER PUBLICATIONS

English machine translation of DE10357505A1, May 19, 2005, EHWA Diamond Industrial Co Ltd.

(Continued)

*Primary Examiner* — Eric A. Gates
(74) *Attorney, Agent, or Firm* — Aird & McBurney LP

(57)          ABSTRACT

The present invention relates to a connection set for connecting a tool to a hand-held machine tool, which consists of, or comprises, a receptacle and an insert. The receptacle is designed provided and/or suitable to be fastened to a machine tool and to receive an insert. The insert is designed, provided and/or suitable for being fastened to the tool and for being releasably, at least in sections, inserted into the receptacle. In this, both the receptacle and the insert are continuous in the longitudinal direction and circumscribe each a lumen. Furthermore, the receptacle comprises one or several stationary pins projecting from an inner wall into the lumen and one or several movable pins. The outside of the insert comprises one or several guides, which are provided, designed or suitable for guiding the pins along the outside of the insert when inserting the insert into the lumen of the receptacle.

21 Claims, 9 Drawing Sheets

(56)                    References Cited

U.S. PATENT DOCUMENTS

|  |  |  |  |  |
|---|---|---|---|---|
| 3,444,781 A | * | 5/1969 | Merle | .................. B23B 31/113 |
|  |  |  |  | 409/218 |
| 3,747,946 A | * | 7/1973 | Edens | ............... B23B 31/10741 |
|  |  |  |  | 279/81 |
| 8,944,069 B2 |  | 2/2015 | Miller et al. |  |
| 9,066,730 B2 |  | 6/2015 | McMinn et al. |  |
| 9,937,009 B2 |  | 4/2018 | Schroeder et al. |  |
| 10,912,597 B2 |  | 2/2021 | Pedicini |  |
| 2019/0151959 A1 |  | 5/2019 | Ho |  |
| 2020/0054354 A1 |  | 2/2020 | Sholev |  |

FOREIGN PATENT DOCUMENTS

| DE | 102011113127 | A1 | 3/2013 |
|---|---|---|---|
| DE | 102019220092 | A1 | 6/2021 |
| EP | 2964109 | B1 | 4/2018 |
| EP | 1850761 | B1 | 2/2020 |
| EP | 2647339 | B1 | 4/2020 |
| WO | 2016199152 | A1 | 12/2016 |
| WO | 2021062548 | A1 | 4/2021 |

OTHER PUBLICATIONS

English machine translation of DE102011113126A1, Mar. 14, 2013, Storz, Olaf.

English machine translation of DE102011113127A1, Mar. 14, 2013, Storz, Olaf.

English machine translation of DE102019220092A1, Jun. 24, 2021, Mapal Fabrik Fuer Praez DR Kress KG.

* cited by examiner

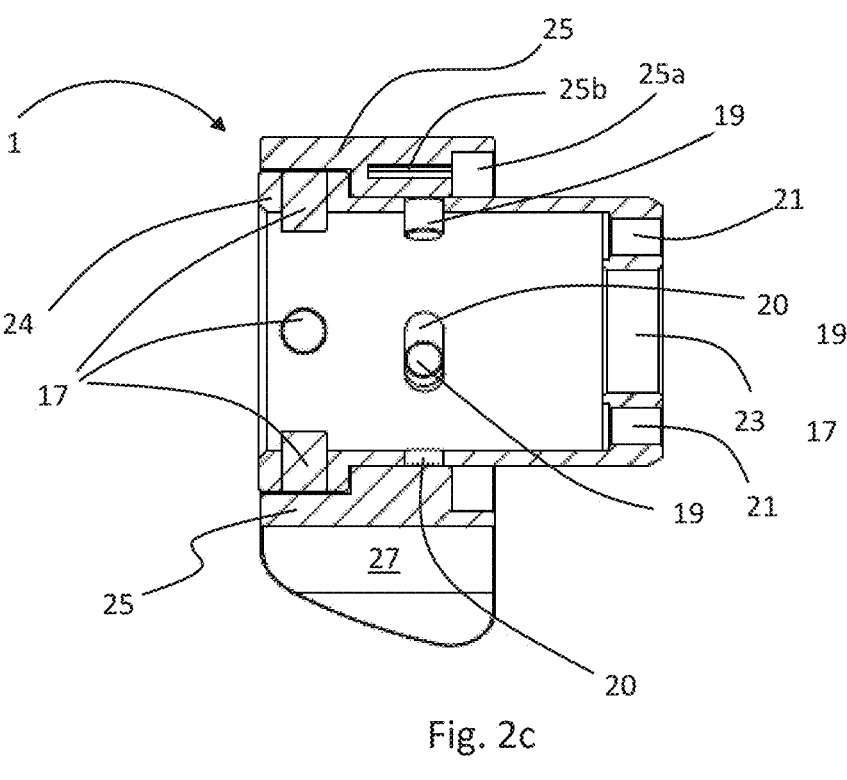
Fig. 2c
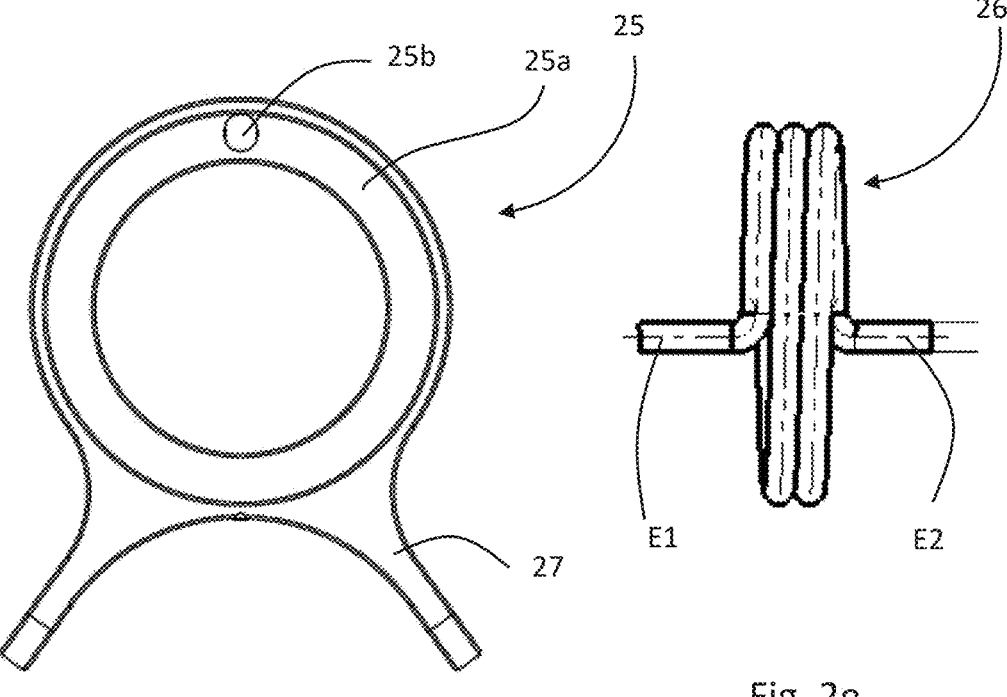
Fig. 2d
Fig. 2e

TOOL QUICK-CHANGE SET FOR MEDICAL HAND-HELD MACHINE TOOL

FIELD OF THE INVENTION

The present invention relates to a connection set, a hand-held machine tool, a tool and a set; it also relates to a method for preparing a machine tool and a method for separating a tool from the machine tool or according to the preambles or generic terms described herein.

BACKGROUND OF THE INVENTION

During operations, particularly in bone surgery, machine tools are used which may receive various tools, for example saws, drills, corrugated wires and similar, or receptacles or adapters thereto and which are preferably battery-operated.

From DE 10 2011 113 126 and DE 10 2011 113 127, each of which was filed by the applicant of the present invention with the German Patent and Trademark Office on Sep. 14, 2011, machine tools are known which are hand-held and are preferably used in medicine (inter alia in surgery or orthopedics). Hereby, their descriptions are incorporated in this description in their entirety by reference and made the subject-matter also of the present invention or disclosure.

SUMMARY OF THE INVENTION

It is an object of the present invention to specify a connection set for connecting a tool to a hand-held, particularly medical or surgical, machine tool.

Furthermore, a hand-held, in particular medical machine tool, a tool and a set as well as a method for preparing a machine tool and a method for separating a tool from the machine tool are to be specified.

The object according to the present invention is achieved by a connection set, by a hand-held machine tool, by a tool and by a set. Furthermore, it is achieved by a method for preparing a machine tool and by a method for disconnecting a tool from the machine tool.

The connection set according to the present invention serves to connect a tool to a hand-held machine tool. It comprises or consists of a receptacle and an insert.

The receptacle is designed, provided and/or suitable to be fastened to a machine tool and for receiving an insert described below.

The insert is designed, provided and/or suitable to be fastened to a tool, which is to be used together with the machine tool, and to be releasably, at least in sections, inserted into the receptacle.

Here, both the receptacle and the insert each circumscribe or encompass a lumen which is continuous in the longitudinal direction of the receptacle or the insert, respectively. In this, the lumens may have diameters between 5 mm and 25 mm, preferably between 10 mm and 20 mm, most preferably between 12 mm and 18 mm, for the insert and between 5 mm and 10 mm for the drive shaft. For example, the fully continuous lumen has a diameter of 8.1 mm and the lumen of the insert has a diameter of 16 mm.

Further, the receptacle comprises one or several stationary pins projecting from an inner wall into the lumen of the receptacle and one or several movable pins.

The movable pins may be directly or indirectly biased or loaded optionally by a spring.

Both the stationary pins and the movable pins project into the lumen of the receptacle.

"Stationary" may be understood herein to mean fixed, non-displaceable, and/or fixed relative to an interior section or interior wall of the receptacle. The movable pins are movable relative to the inner section or to the inner wall. Alternatively, the stationary pins may also be movable relative to the inner section or to the inner wall, but then preferably to a lesser extent or in a more spatially restricted manner than the movable pins.

The insert comprises a link guide or guide on its outside, by which the pins are guided along the outside of the insert when the insert is inserted into the lumen of the receptacle.

In this, the pins have diameters of 2 mm to 4 mm, for example. The stationary pins, which may have the same, a larger or a smaller diameter than the movable pins, preferably have a diameter of 3 mm, while the movable ones preferably have a diameter of 2.5 mm. The guides, e.g. designed as grooves preferably opening outwards in the wall of the insert, have widths corresponding at least in sections to the diameters of the pins to be received in them, preferably 3.1 mm and 2.6 mm. Their lengths are limited, for example, by the geometry of the insert The present invention further relates to a hand-held medical machine tool or non-medical machine tool having at least one receptacle as described herein.

Further, the present invention relates to a medical tool or non-medical tool for use with a hand-held machine tool connected to at least one insert as described herein.

When reference is made herein to a "tool", then such tool may be or comprise a tool such as a saw, drill, Kirschner wire or similar, and/or an attachment and/or adapter for such tool, for example a chuck for a tool such as a drill or a Kirschner wire or the like.

The present invention further relates to a set comprising or consisting of a hand-held machine tool according to the present invention, at least one tool according to the present invention and at least one connecting set according to the present invention.

The present invention further relates to a method for preparing a machine tool for the use thereof.

The method for preparing a machine tool according to the present invention encompasses the following steps:

provide a hand-held machine tool;

providing a tool for the machine tool;

providing a connection set according to the present invention;

preferably: connecting the receptacle of the connection set to the machine tool;

preferably: connecting the insert of the connection set to the tool; and optionally:

connecting the insert to the receptacle by inserting the insert, at least in sections, into the lumen of the receptacle.

Connecting the receptacle of the connection set to the machine tool and connecting the insert of the connection set to the tool may, in some embodiments, have already been taken place prior to the method according to the present invention, for example at the factory during the manufacture of the machine tool and the tool or prior to their first commissioning or implementing.

The present invention further relates to a method for separating a tool from a machine tool. This method encompasses the following steps:

providing a machine tool, which has been connected to a tool in accordance with the method according to the present invention for preparing a machine tool for the use thereof;

moving the movable pins, and if they are biased or loaded by a spring, against the effect of the spring;

removing the tool from the machine tool by pulling on the tool, alternatively or additionally with the aid of gravity.

All the advantages achievable with the methods according to the present invention may, in certain embodiments according to the invention, also be achieved undiminished with the devices according to the present invention, and vice versa.

Embodiments according to the present invention may comprise some, several or all of the following features in any combination, unless the person skilled in the art recognizes their combination as technically impossible. Advantageous developments of the present invention are each subject-matter of the dependent claims and embodiments.

In all the following statements, the use of the expression "may be" or "may have" and so on, is to be understood synonymously with "preferably is" or "preferably has," and so on respectively, and is intended to illustrate embodiments according to the present invention.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" (also "a/an") as encompassing "at least one". This understanding is also equally encompassed by the present invention as the interpretation that a numeric word, for example, "one" (also "a/an") may alternatively mean "exactly one", wherever this is evidently technically possible for the person skilled in the art. Both understandings are encompassed by the present invention and apply herein to all used numerical words.

Whenever spatial information, such as e.g. "top", "bottom", "left" or "right" is mentioned herein, the person skilled in the art understands this to mean the arrangement in the herein-attached figures and/or in the state of use. "Bottom" is closer to the center of the earth or the bottom of the figure than "top".

Advantageous developments of the present invention are each subject-matter of the dependent claims and embodiments.

Whenever an embodiment is mentioned herein, it is then an exemplary embodiment according to the present invention When it is disclosed herein that the subject-matter according to the present invention comprises one or several features in a certain embodiment, it is also respectively disclosed herein that the subject-matter according to the present invention does, in other embodiments, likewise according to the present invention, explicitly not comprise this or these features, for example, in the sense of a disclaimer. Therefore, for every embodiment mentioned herein it applies that the converse embodiment, e.g. formulated as negation, is also disclosed.

In some embodiments, the inner section of the receptacle is cylindrical in shape in order to receive an insert, such as a cylindrical insert. In other embodiments, the inner section may be differently shaped or comprise differently shaped sections, for example, the shape of a cone or cone section. The cone shape may be present e.g. on an outer surface, e.g. of the insert, and/or on an inner surface, e.g. of the receptacle.

A geometry such as that of the so-called hollow shank taper may be provided.

In several embodiments, the insert comprises a flange at one of its ends, which may be provided, designed and/or suitable for facilitating connection of the insert to the tool. It may also serve as a stop that axially limits the depth to which the insert is inserted into the receptacle. It may thus be part of a geometric design which enables or ensures play-free reception of the insert in the receptacle, at least in the axial direction or longitudinal direction.

In some embodiments of the connection set according to the present invention, the guide on the outside of the insert tapers in a first section starting from a first end of the insert towards a second end of the insert opposite the first end, for example in a funnel-like manner. Preferably, the guide tapers only or exclusively in this section, i.e. it does not become wider again in its course.

The guide preferably starts at the outermost front end face of the insert. The end front face of the insert—which is the first to be inserted into the receptacle when the insert and receptacle are connected to each other—or the wall of the insert thus respectively have, in some embodiments, at the outermost front end face at least two widths or thicknesses, a, respectively, smaller one namely where (in the axial direction) the guide already begins at the front end face, and a thicker one namely where no guide yet begins. In some embodiments, the section of the outer circumference of the front end face where the guide already begins is greater than where the guide does not yet begin (but continues axially toward the flange or opposite end). In several embodiments, the ratio of the proportion of these thicker sections relative to the circumference to the proportion of these thinner sections is 1:10 or less. The lower this ratio, the easier it is for the insert arbitrarily inserted into the receptacle to orient itself in the circumferential direction toward the desired rotational position already as it begins to be inserted into the receptacle.

In several embodiments, the first section of the guide on the outside of the insert merges, indirectly or directly, into a second section which does not taper, but preferably has mutually parallel sides or parallel side walls, or parts thereof, at least in sections.

The distance between the parallel sides or side walls, or sections thereof, is preferably just large enough to allow the pins to be guided in the insert, e.g. without play or with predetermined play.

In some embodiments of the second section, the average distance between the sides or side walls, whether parallel to each other or not, and/or the average width of the second section, is less than the average width of the first section.

Preferably, the second section extends along or parallel to a longitudinal axis or longitudinal central axis of the insert.

In some embodiments, the guide comprises a third section which is at an angle of at least 15° at least 30° and/or at most 90° to the longitudinal axis or longitudinal central axis of the insert and/or to a longitudinal extent of the second section. The third section preferably extends both circumferentially and toward the flange or tool connected to the insert, and thus away from the free, front end side of the insert.

In several embodiments of the connection set according to the present invention, the inner wall is part of an inner section of the receptacle.

In some embodiments, the receptacle comprises a device or mechanism designed, provided and/or suitable for biasing or loading the one or several movable pins by one or several springs. This mechanism is preferably not manually operable and/or does not need to be operated to connect the insert and receptacle to each other, but may need to be operated to disconnect the insert from the receptacle.

In some embodiments, the connection set comprises a device or mechanism designed, provided and/or suitable for moving the one or several pins biased or loaded—directly or indirectly—by a spring against the effect of the spring. This mechanism may be provided in the form of an outer section or a rotating ring.

Thus, the movable pins may in turn be provided stationary on e.g. the outer section, described in more detail below, which may be arranged to be movable relative to the inner section and, in its movement about, or relative to, the inner section, entrains in its rotational movement the pins which are stationary thereon and relative thereto, and therefore these pins are herein considered to be movable, relative to the inner section.

In several embodiments, each pin may be acted upon by its own spring, thus multiple springs may be provided.

However, in some embodiments, the outer section or rotating ring is biased or preloaded by a spring; in this, the movable pins are only indirectly biased or loaded (by the spring of the outer section).

In some embodiments, the device or mechanism for moving the pins is, or comprises, an outer section or rotating ring. The outer section or rotating ring is provided to be rotatable relative to the inner section, which comprises the inner wall.

In several embodiments of the connection set, the inner section has at least one passage opening for guiding the movable pins at least also in a radial direction.

In some embodiments, the at least one passage opening does not taper, but preferably comprises mutually parallel sides and/or side walls, or sections thereof, at least in sections.

In several embodiments, the receptacle of the connection set according to the present invention comprises a fastening section for fastening it to the machine tool and a free end for receiving the insert. In this, in some embodiments, at least one of the stationary pins projecting into the lumen of the receptacle is arranged closer to the free end than at least one of the movable pins. In other embodiments, at least one of the stationary pins projecting into the lumen of the receptacle is arranged further from the free end than at least one of the movable pins. In yet other embodiments, at least one of the stationary pins projecting into the lumen of the receptacle is arranged at the same height relative to the free end as at least one of the movable pins.

In some embodiments, the guide of the insert in interaction with the movable pins and the stationary pins of the receptacle effects the insert to be received in the receptacle without axial and/or radial play.

In several embodiments of the connection set, the longitudinal axis of the through-opening for the movable pin is at an angle greater than 0° with respect to the longitudinal axis of the third portion of the guide in order to cause jamming of the movable pin in the axial direction and/or in the circumferential direction.

In some embodiments, the geometric configuration of the guide, in particular of the first section of the guide 35$a$, of the insert causes the insert to self-align when inserted into the receptacle.

In several embodiments, by the interaction of the guide of the insert with the pins of the receptacle, only the mere application of force in the axial direction, or preferably only in the axial direction is necessary for inserting the insert into the receptacle. In particular, no use of tools and/or no actuation or triggering of a mechanism, switch, or similar is required.

In some embodiments, the machine tool according to the present invention comprises at least one power unit, which can be provided to be releasably received in the machine tool.

In several embodiments, the power unit of the machine tool comprises at least one power source, a power consumer, such as a motor, and/or a switching device. The switching device may itself be or comprise a circuit board.

In some embodiments, the power unit comprises a device for controlling and/or regulating the motor of the power unit.

In several embodiments, the machine tool comprises at least one shaft and/or gearbox respectively connected to the motor.

In some embodiments, the tool is a drill, a saw, or an oscillating saw, or a jigsaw, or a sagittal saw.

In several embodiments, the machine tool comprises an actuator element for the actuation by a user to retrieve power from the power source for operating the machine tool.

In some embodiments, it is provided that the movable pins cannot arrive at or move into the terminating region of the end of the third section, but rather the third section is sufficiently long such that the movable pins jam against the wall of the third section before reaching the end of the third section.

In several embodiments, the third section on the one hand and the inner through-opening of the outer section on the other hand have longitudinal axes or unwindings of their longitudinal axes that differ from each other. The longitudinal axes or unwindings may differ from each other in that they are at different angles to the longitudinal direction of the connection set or to the circumferential direction of the connection set, and/or in that they do not run or extend parallel or identical to each other. Preferably, the longitudinal axis of the third section is such that the end of the third section is closer to the optional terminating flange than some or all of the other sections of the third section, for example, in a side view or in an unwinding.

In some embodiments, at least one component or section or surface of a component comprises a coating. The coating may be selected to reduce or minimize friction, particularly sliding friction.

For example, a coating may be provided on the outside of the inner section and/or on the inside of the outer section. It may preferably facilitate twisting of the outer section relative to the inner section.

Instead of such a coating, or in addition thereto, a device may be provided which also facilitates twisting or movement of two components relative to each other, such as the first section relative to the second section. Such a coating may be, or encompass a bearing, wherein roller bearings, needle bearings, and more are contemplated therefor.

In several embodiments, the pins are elevations or projections. In some embodiments, they are integrally made with, for example, the inner section or the outer section, respectively, in others, they are joined thereto, for example, by interference or press fit, welding, etc.

Some or all of the embodiments according to the present invention may have one, more or all of the advantages mentioned above and/or below.

One advantage of the present invention may be that a wide variety of tools or tool attachments (for example, a drilling attachment or drilling chuck, sawing attachments, or a Kirschner wire chuck) may be connected to the machine tool. In this way, the machine tool becomes a multifunctional power tool (e.g. for bone surgery).

No other tool is required for connecting or disconnecting the tools to or from the machine tool. This may represent a further advantage of the present invention.

Advantageously, no manual unlocking of the receptacle is further necessary for preparing the insertion of a tool. Said tool only has to be inserted with force. Due to the advantageous geometrical design of the present invention, a tool equipped therewith may be pushed on at any desired angle of rotation. The present invention finds by itself the appropriate orientation of the tool for connection to the machine tool. The guide or link guide provides the required rotation about the longitudinal axis. Locking of the tool after insertion is likewise automatic, as the movable pins find their way into the third section of the guide, for example, spring-driven. This enables simplified handling of the machine tool and the tools and may constitute a further advantage of the present invention.

A further advantage of the present invention may be that the tool no longer has any unwanted axial or radial play after it has been—automatically—locked. This enables more precise handling of the tool, which indirectly contributes to patient safety.

Advantageously, the tool may be separated from the machine tool again via a manual rotary movement of the rotating ring. Advantageously, this may be done with one hand. This in turn enables simplified handling of the machine tool and tools, and may represent a further advantage of the present invention.

BRIEF DESCRIPTION OF THE DRAWINGS

In the following, the present invention will be described with reference to the accompanying figures purely exemplarily. In them, the same reference numerals denote identical or similar components. The following applies:

FIG. 2c shows the receptacle of FIG. 2a in longitudinal section through the illustration of FIG. 2a;

FIG. 2d shows the outer section of the receptacle of FIG. 1 to FIG. 2c from the rear, i.e. looking from the side of FIG. 2a facing away from the user;

FIG. 2e shows a torsion spring from the spring mechanism, which is used when the connection set or its receptacle is connected to the machine tool;

DETAILED DESCRIPTION

Figure 1:
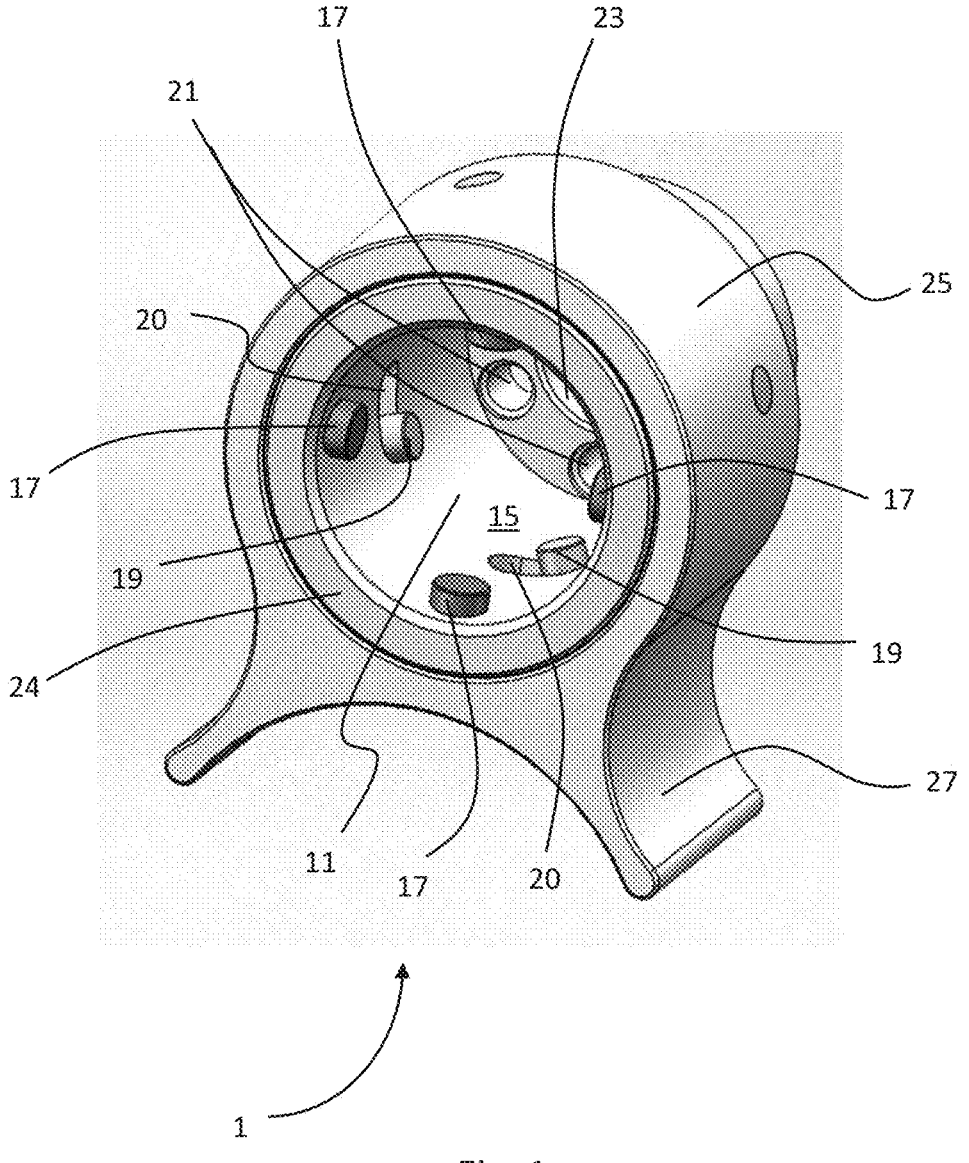
FIG. 1 shows a receptacle having an outer section or rotating ring in a first embodiment of the connection set according to the present invention.

FIG. 1 shows a receptacle 1 of a connection set 100 according to the present invention of a first embodiment. The receptacle 1 is shown facing its end, referred to herein as the free end, while a fastening section of the receptacle 1, which serves to attach said receptacle 1 to the machine tool 4 (see FIG. 3 and FIG. 5), faces away from the viewer of FIG. 1.

The receptacle 1 comprises an inner section 24, e.g. a cylindrical section, which, facing its outside, carries or is surrounded by an outer section 25, here optionally designed as a cylindrical section, in the form of a rotating ring.

The inner section 24 is designed, provided and/or suitable for releasably receiving an insert 3, not shown in FIG. 1.

The outer section 25 (in the following also referred to as the rotating ring 25) optionally comprises, for example on its underside, one or several finger sections 27, projections or grips on which force may be applied by a finger of a hand to rotate it about the longitudinal axis of its lumen 11 or receptacle section.

The effect of such rotational movement is described in more detail with reference to FIG. 2a and FIG. 2b.

The inner section 24 comprises, here exemplarily four, stationary or immovable pins 17 relative to the inner section 24, which project from an inner wall 15 of the inner section 24 into its lumen 11. Optionally, two of them lie each opposite to each other and/or lie opposite to each other with respect to a cross-section through the receptacle 1.

The rotating ring 25 comprises, preferably as many, here four (of which only two can be seen in FIG. 1), pins 19 designated herein as movable, which engage through—e.g. elongated—passage openings 20 of the inner section 24 or project into the lumen 11, respectively.

The outer section 25 may be spring-biased or preloaded by springs and assume a corresponding rotational position. It serves as a mechanism or device for moving the movable pins 19 circumferentially, for example against the effect of the spring(s) acting on it, not shown here.

Figure 2A:
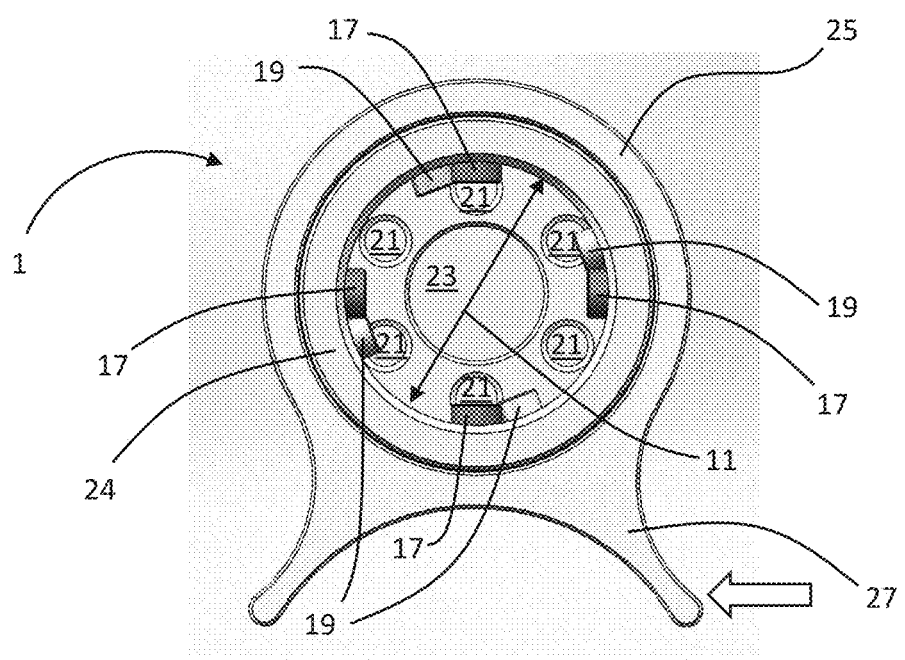
FIG. 2a shows the receptacle of FIG. 1 from the front in its locked state or connected state.
Figure 2B:
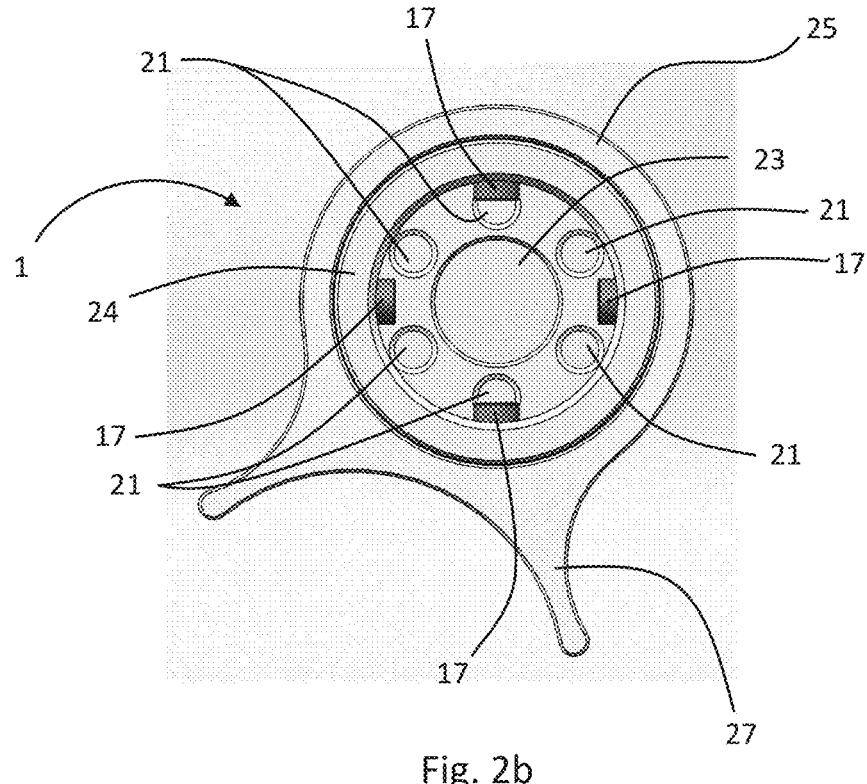
FIG. 2b shows the receptacle of FIG. 1 from the front in its open state or state ready for releasing the insert from the receptacle.

The position of the movable pins 19 relative to the stationary pins 17 is discussed in more detail in the description with regard to FIG. 2a and FIG. 2b.

The number, position and distribution of pins 17, 19 is purely exemplary and should not be understood as limiting. Both an even number and an odd number of pins 17 and/or pins 19 are encompassed herewith.

On the rear side or rear front end face of the inner section 24, i.e. facing away from the viewer of FIG. 1, the inner section 24 optionally comprises screw passages 21, here exemplarily six, of which only two can be seen in FIG. 1. These optionally serve here for connecting the receptacle 1 to a hand-held machine tool 4 (hereinafter in short: machine tool), as shown for example in FIG. 3, using screws. Other connection methods such as welding etc. are also possible.

A passage for a shaft coupling 23 is provided centrally on the rear side of the inner section 24. The shaft coupling 23 may project into the lumen 11.

The pins 17, 19 can each be pushed from the outside through bores in the wall of the inner section 24 and outer section 25, respectively, so that they project sufficiently inwardly. In this position, the stationary pins 17 may be fixed to the inner section 24, for example by welding, gluing, etc., and the movable pins 19 may be fixed to the outer section 25, for example by one of the methods mentioned.

Where pins are referred to herein, projections, dowels, etc. may alternatively be provided.

FIG. 2a shows the receptacle 1 of FIG. 1 from the front in its locked state or connected state. In this state, which is characterized by the position of inner section 24 and rotating ring 25 relative to each other, an insert 3 inserted into receptacle 1 could not be removed or pulled out of receptacle 1.

Reference is made to the description with regard to FIG. 1.

FIG. 2a shows the outer section or rotating ring 25 with its finger section 27. The inner section 24 comprises, as already explained above, exemplarily four stationary pins 17, which in the example of FIG. 2 are optionally distributed equidistantly radially on the inner side of its lumen 11 or receiving section.

The pins 19, which are also spring-loaded indirectly via the spring loading of the rotating ring 25, protrude (e.g. in a cross-section) from behind the stationary pins 17 in the locked state, which can be seen in FIG. 2a. This shift of the movable pins 19 relative to the stationary pins 17 effects in addition to the radial locking by the stationary pins 17 an axial locking of the insert 3, not shown in FIG. 2b, and, therefore, indirectly the locking of a tool 5, non-rotatably connected to it, within the receptacle 1. The tool 5 is thus connected to the machine tool 4 during use by the position of the rotating ring 25 preferably both radially and axially without play, but can nevertheless be easily separated from it, if necessary, as explained below.

If force is applied manually, generally by the thumb, to the finger portion 27 of the rotating ring 25 (shown by an arrow in FIG. 2a), the rotating ring 25 rotates about the inner section 24 preferably to such an extent that the open state of FIG. 2b is reached. The length and shape of the passage openings 20 for the movable pins 19 may be designed as a stop, which ensures an optimum limitation of rotational movement.

FIG. 2b shows the receptacle 1 of FIG. 1 from the front in its open state.

The statements made with regard to FIG. 1 and FIG. 2a also apply analogously to FIG. 2b. Reference is therefore made to these statements in order to avoid repetition. In the following, only the differences will be discussed.

The movable pins 19 are not visible in the open state, since they flush with the stationary pins 17 when viewed from the front of the receptacle 1 or in a cross-section close to the drawing plane, i.e. they are concealed by them.

The effect of this arrangement is that the tool 5 is now no longer locked axially and may be easily separated from the machine tool 4 (see FIG. 5), advantageously with only one hand, by moving it in the axial direction (manually or by gravity).

FIG. 2c shows the receptacle 1 of FIG. 2a in longitudinal section.

The outer section 25 encompasses the left half of the inner section 24 over its entire circumference. The inner section 24 is secured axially against falling out or being pulled off by the movable pins 19, which extend from the outer section 25 through the passage openings 20 into the lumen 11 of the inner section 24.

On its rear side, i.e. on the right in FIG. 2c, the outer section 25 comprises a groove, e.g. a groove 25a running radially around its edge, and optionally a bore 25b for receiving a torsion spring 26 (see FIG. 2e).

As in the previous figures, the stationary pins 17 are also clearly visible here. Furthermore, at the right end of the inner section 24, the passage 23 for the shaft coupling and the screw passages 21 can be seen.

FIG. 2d shows the outer section of the receptacle of FIG. 1 from the rear, i.e., looking from the side of FIG. 1 facing away from the user. There is no inner section 24 inserted in the outer section 25 in the illustration of FIG. 2d.

A view to the rear side of the outer section 25 shows a view of the optional circumferential groove 25a, for holding a torsion spring 26 (see FIG. 2e) or another spring, and the bore 25b for the torsion spring 26 (see again FIG. 2e).

FIG. 2e shows a torsion spring 26 from the spring mechanism, which is used when the connection set 100 is connected to the machine tool 4.

The shown torsion spring 26 is arranged in the circumferential groove 25a such that the first end E1 of the torsion spring 26 engages in the bore 25b in the outer section 25. The second end E2 is inserted into a corresponding bore in or on the machine tool 4, and the receptacle 1 is connected to the machine tool 4.

When the outer section 25 is rotated by pressure on the finger section 27 against the spring force of the torsion spring 26, the movable pins 19 take their place in alignment with the stationary pins 17 (see FIG. 2b). An insert 3, if connected to the receptacle 1, could be removed from the receptacle 1 again in this state. If the force is no longer applied to the finger section 27, the spring force of the tensioned torsion spring 26 effects the outer section 24 and thus the movable pins 19 to be returned back to the locked state (see FIG. 2a).

The torsion spring 26 further effects that insertion of the insert 3 into the receptacle 1 of the connection set 100 may take place without exerting a force on the finger section 27 of the outer section 25. The geometry of the guide 35 on the insert 3 pushes the movable pins 19 within or along the passage openings 20 to the side against the spring force of the torsion spring 26, and the restoring spring force then effects the movable pins 19 to find their way into the third section 35c of the guide 35 and to be axially locked there.

Figure 3:
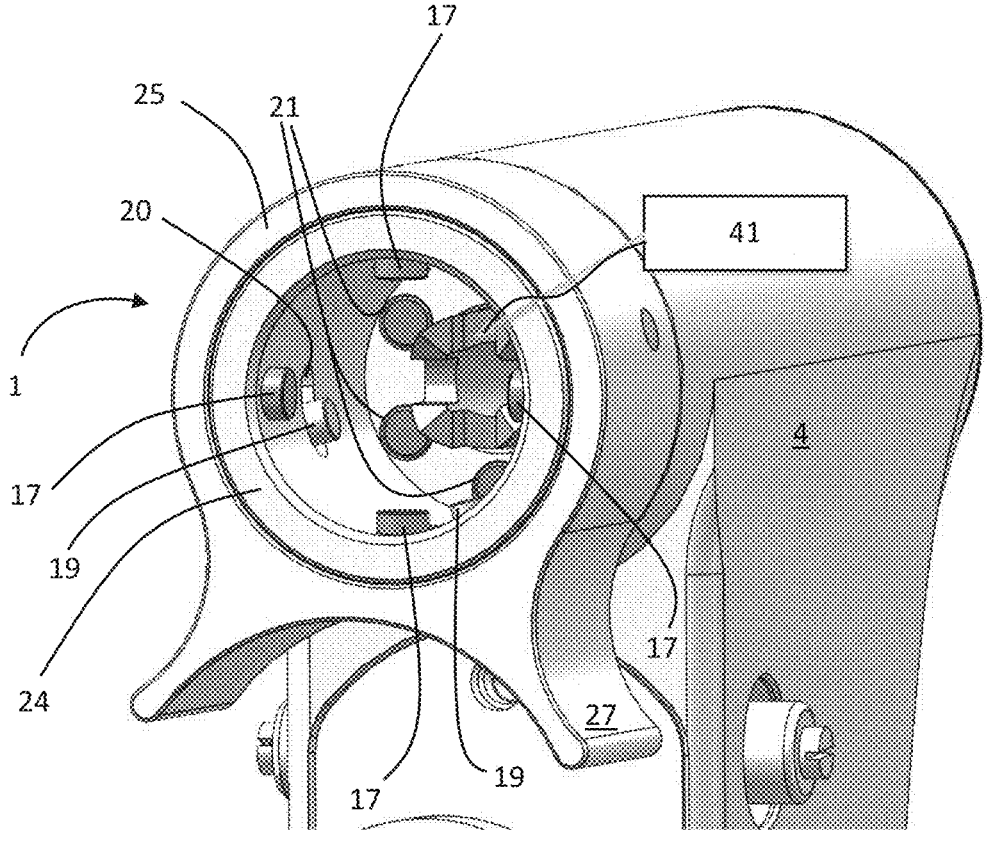
FIG. 3 receptacle of FIG. 1 mounted on a machine tool in a locked state from an oblique front view.

FIG. 3 shows the receptacle 1 of FIG. 1 from an oblique front view, mounted on a machine tool 4 in the locked state.

The machine tool 4 may, in some embodiments, comprise or be connected to a power source or voltage source. It may further comprise a power consumer, for example a motor, and a switching device. The power consumer may be connected to and also disconnected from the power source using the switching device.

The machine tool 4 may further comprise openings configured, provided and/or suitable for receiving screws extending through the screw passages 21 of the inner section 24. These openings of the machine tool 4 may be, for example, blind openings each having an internal thread. The screw connection serves to connect the receptacle 1 to the machine tool 4. This type of connection is in no way to be understood as limiting, other types of connections at this point are also encompassed by the present invention.

The machine tool 4 further comprises a shaft coupling 41, which extends through the passage 23 for the shaft coupling 41 on the rear side of the inner section 24. The shaft coupling 41 is configured, provided and/or adapted to transmit torque from the shaft coupling 41 to a shaft of the tool 5.

The shaft coupling 41 does not approach the edge of the receptacle 1, i.e. the free end of the shaft of the shaft coupling 41 ends in the lumen of the receptacle 1 before the opening plane thereof.

Figure 4A:
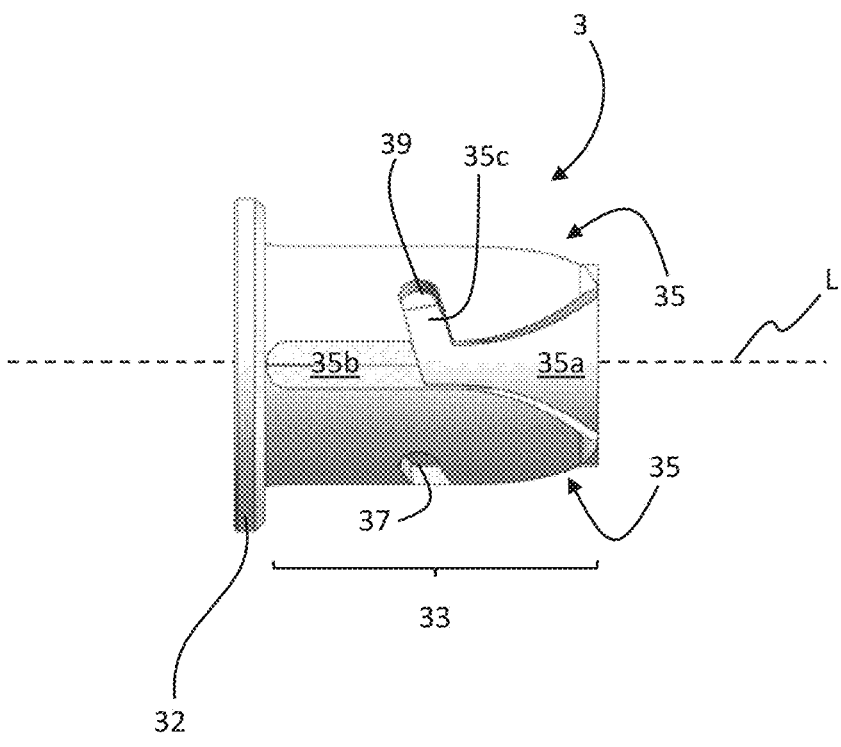
FIG. 4a shows a side view of an insert for a tool.

FIG. 4a shows a side view of an insert 3 for a tool 5.

Figure 5:
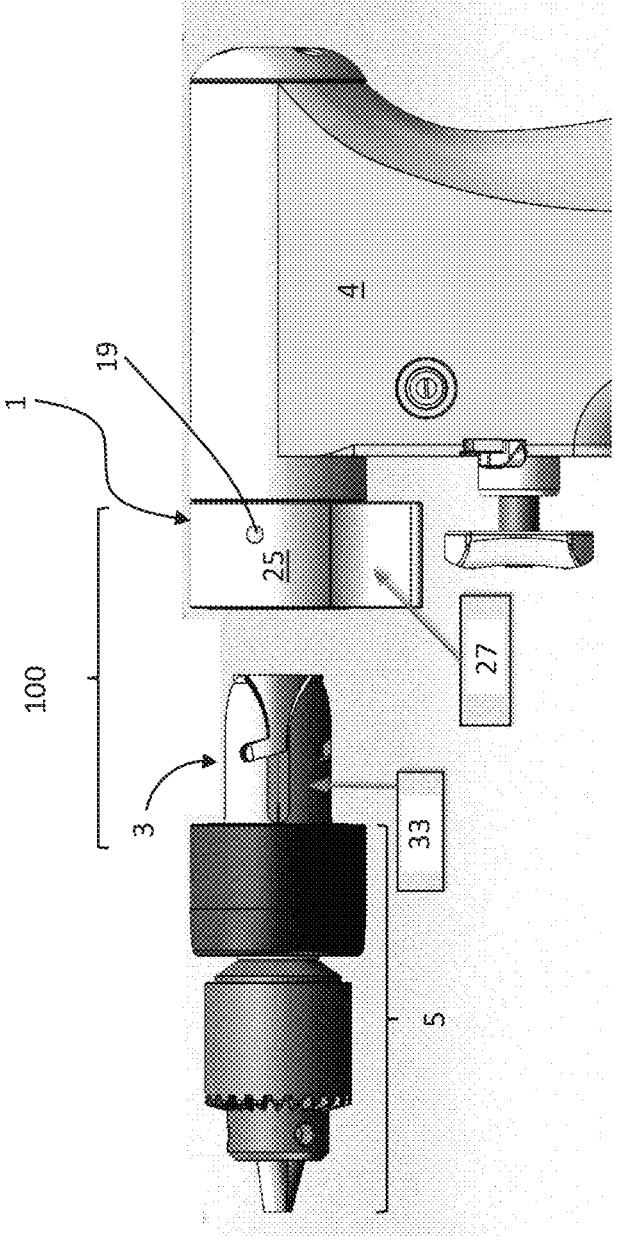
FIG. 5 shows the connection set according to the present invention with the receptacle of FIG. 1 mounted on a machine tool together with a tool, here a drill chuck, provided with the insert of FIG. 4.

The insert 3 is optionally designed at one of its ends (left in FIG. 4a) as or with a flange 32, which is provided and/or suitable to be, or become, during use connected, preferably non-releasably, to the tool 5 (to be connected to the machine tool 4) (see FIG. 5 left). This connection may be made, for example, by welding or any other type of releasable (screw connection, snap-in connection, etc.) or non-releasable connection. The end referred to herein as the free end or front end side is on the right relative to FIG. 4a.

The insert 3 comprises a sleeve section 33 which comprises a continuous lumen 31.

Furthermore, on the outside of the sleeve section 33, the insert 3 comprises one or several link guides or guides 35, here in the form of grooves, ideally as many as stationary pins 17 are arranged in the inner section 24 or as movable pins 19 are arranged in the outer section 25 of the receptacle 1, here, hence, exemplarily four. The guide 35 extends from a first end of the insert 3, here the end facing away from the flange 32, towards a second end of the insert 3 opposite the first end, here the end optionally configured as the flange 32.

The guide 35 comprises as a first section 35a in the direction of the end facing away from the flange 32 a tapering section, here a tapering groove, which preferably only tapers, i.e. does not become wider again in its longitudinal extent. The first section 35a of the guide 35 merges directly or indirectly into a second section 35b of the guide 35, which does not taper further but preferably comprises sides parallel to each other at least in sections up to its end. The distance between the parallel sides of the second section 35b is preferably just large enough to be able to guide the pins 17, 19 in the insert 3, for example without play or with predetermined play, for example, in that the groove of the second section 35b for receiving the pin 17, 19 is dimensioned, for example, 10% larger than the pin 17, 19.

The guide 35 further comprises a third section 35c, which is at an angle of at least 15° to a longitudinal axis L of the insert 3 and/or to a longitudinal extension of the second section 35b of the guide 35 and which optionally ends in an end 39.

Due to the arrangement of the guide 35, the angular position of the insert 3 or of the tool 5 provided with or connected to the insert 3 is any arbitrary position relative to the rotating ring 25 at the beginning of the insertion.

The tapers of the first sections 35a of the guide 35 ensure that the insert 3 or the tool 5 automatically aligns itself within and relative to the receptacle 1 in a direction of rotation as the insert 3 is increasingly inserted into the lumen 11 of the receptacle 1, and ultimately the stationary pins 17 are received in the second section 35b of the guide 35 and thereby effects the insert 3 or the tool 5 connected therewith, respectively, to be radially locked in the receptacle 1.

When the insert 3 is pushed into the receptacle 1, the movable pins 19 first recede behind the stationary pins 17 against the effect of the spring due to the side surfaces of the taper of the first section 35a of the guide 35, i.e. they optionally finally flush therewith. However, due to the spring force acting on them, they deviate during insertion along the third section 35c of the guide 35 and lock themselves automatically to the respective walls of the third section 35c, mostly to that wall of the section 35c which is more remote from the flange 32. This has the effect that, when the insert 3 is pushed into the receptacle 1, the flange 32 of the insert 3 flushes against front end sided structures of the receptacle 1, in this case the inner section 24. This ultimately has the effect that the tool 5 is locked axially in the receptacle 1. For this purpose, it is provided that the movable pins 19 preferably cannot end up in the terminating region of the end 39, but that the end 39 forms a remaining travel reserve for the movable pins 19.

Figure 4B:
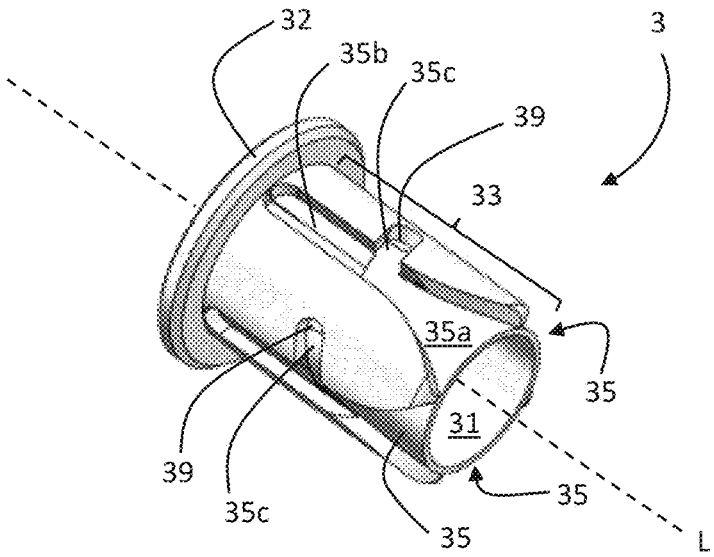
FIG. 4b shows the insert of FIG. 4a in perspective view.

FIG. 4b shows the insert 3 of FIG. 4a in perspective view looking from the right at the front end face, which reveals different wall thicknesses of the insert 3.

The statements made with regard to FIG. 4a also apply analogously to FIG. 4b. Reference is therefore made to these explanations in order to avoid repetition.

FIG. 5 shows the connection set 100 according to the present invention.

On the right, FIG. 5 shows the receptacle 1 of FIG. 1, which is fixedly mounted on a machine tool 4. Of the receptacle 1, the outer section 25 and its finger section 27 are visible in the perspective of FIG. 5. Furthermore, a site may be seen where one of the movable pins 19 has been arranged in or on the outer section 25.

On the left, FIG. 5 shows a tool 5, here exemplarily a drill chuck, which is connected to the insert 3 of the connection set 100 according to the present invention.

The above statements made with regard to FIG. 1 to FIG. 4b also apply analogously to FIG. 5. Reference is therefore made to these statements in order to avoid repetitions.

The insert 3 of the connection set 100 according to the present invention could here be connected to the receptacle 1 of the connection set 100 according to the present invention radially and axially without play as described above in order to obtain a reliable tool which could be easily disassembled again, preferably with one hand.

The length of the sleeve section 33 of the shaft coupling 41 may be greater than the depth of the outer section or rotating ring 25, as shown for example in FIG. 5.

The inner section 24 preferably has a, for example small, projection in the axial direction (left-right direction in FIG. 5) with respect to the outer section 25, as can be seen, for example, in FIG. 2c by comparing the extent of the respective left ends, of the sections 24 with 25. In this way, the outer section 25 may be freely rotated, while the inner section 24, e.g. with its flange 32, may flush against rotating ring 3 in the axial direction in a rotationally fixed manner.

Figure 5A:
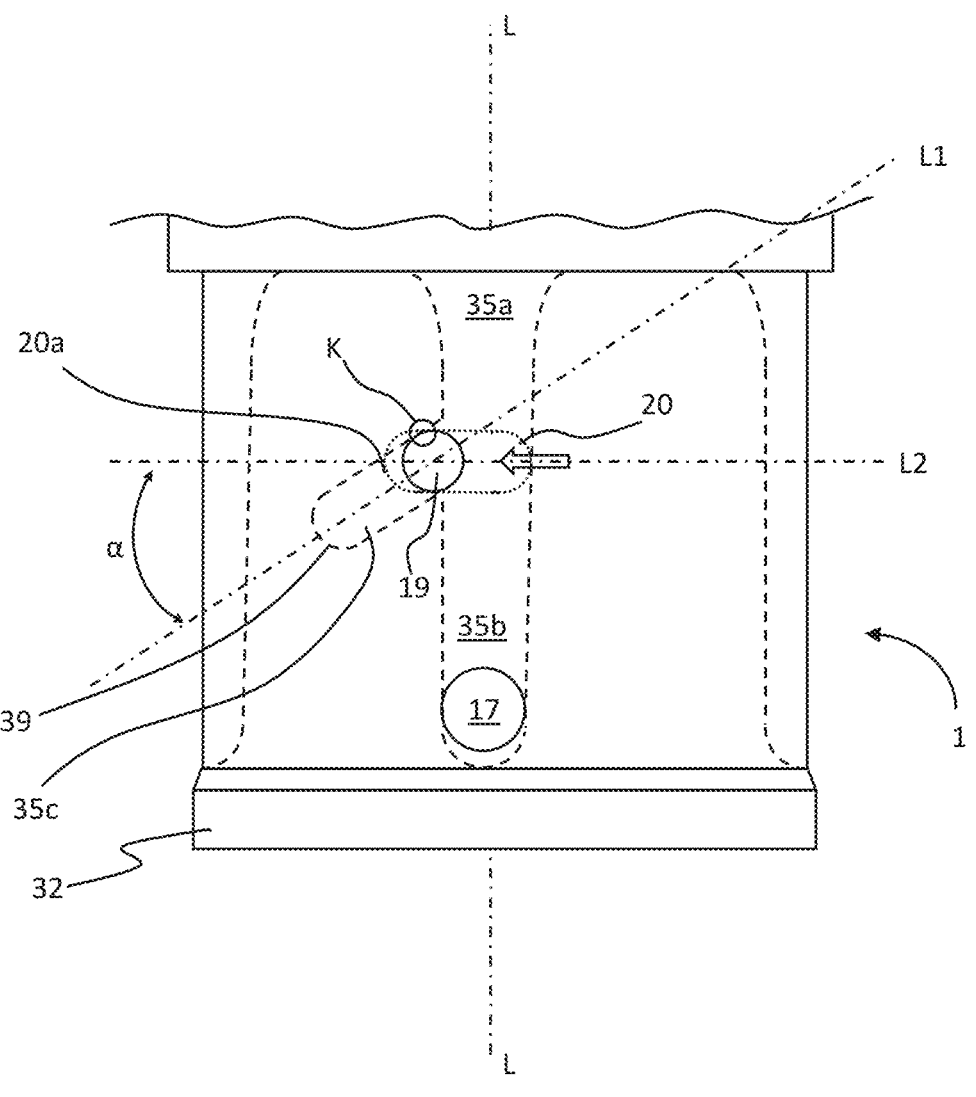
FIG. 5a shows a section of a connection state after connecting the components shown in FIG. 5.

FIG. 5a shows a section of a connection state after connecting the components shown in FIG. 5.

For the sake of illustration, a part of the outer section 25 facing the viewer is not shown. In this way, the view is unobstructed to the sections 35a, 35b and 35c of the guide 35, to a movable pin 19 in its through-opening 20, and to a section of a stationary pin 17.

The movable pins 19, when the insert 3 is pushed into the receptacle 1, are first moved back behind the stationary pins 17 against the action of the spring due to the side surfaces of the taper of the first section 35a of the guide 35, i.e. they optionally finally flush therewith, as described above. However, due to the spring force acting on them (shown in FIG. 5a by means of an arrow), they have in the meantime moved along the third section 35c of the guide 35 during the insertion and lock themselves automatically against the respective walls of the section 35c, mostly against that wall of the section 35c which is more remote from the flange 32, which is underlined here by a drawn circle as contact site K. It can be seen that in this embodiment the movable pins 19 cannot arrive or move into the terminating region of the end 39, but clamp themselves before reaching the end 39. In this case, the movable pins 19 also maintain a distance from the end 20a of the passage opening 20.

The mutually deviating longitudinal axes L1 and L2 (to be considered in circumferential direction or their unwinding, if necessary) of the third section 35c of the inner section 24 or of the passage opening 20 of the outer section 25, respectively, are at an angle α not equal to 0° to each other. This arrangement of the third section 35c and the through-opening 20 with respect to each other ensures a locking without play in this embodiment example. Preferably, the longitudinal axis L1 of the third section 35c is such that the end 39 of the third section 35c is closer to the optional, terminating flange 32 than some or all of the other subsections of the third section 35c, as can be seen in FIG. 5a.

Figure 6:
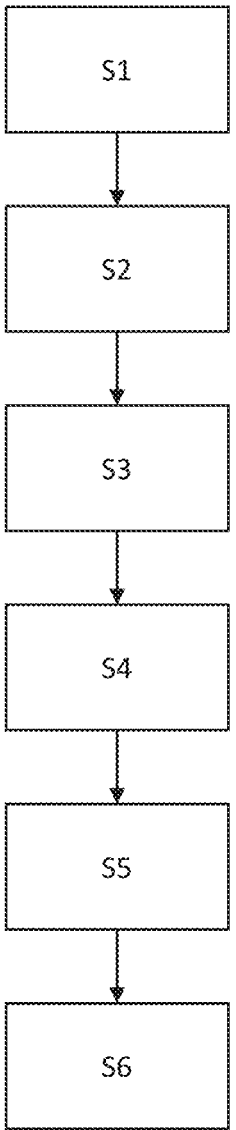
FIG. 6 shows a course of the method according to the present invention for preparing a machine tool for use in an exemplary embodiment.

FIG. 6 shows a course of the method according to the present invention for preparing a machine tool 4 for use in an exemplary embodiment. Reference is made to the descriptions with regard to FIG. 1 to FIG. 5.

Step S1 stands hereby for a preparation of a hand-held machine tool 4.

Step S2 stands for providing a tool 5 for the machine tool 4.

In step S3, a connecting set 100 according to the present invention is provided.

Connecting the receptacle 1 of the connection set 100 to the machine tool 4 is represented by step S4, and connecting the insert 3 of the connection set 100 to the tool 5 is represented by step S5.

Finally, in step S6, the insert 3 is connected to the receptacle 1. This is done by inserting the insert 3, at least in sections, into the lumen 11 of the receptacle 1.

The course of the method steps here is exemplary and is not to be understood as limiting. In some embodiments, said steps may also be performed in a different order. They may be sequential, parallel or overlapping steps in certain embodiments.

In some alternative embodiments, the method begins with step S6. Steps S1 to S5 preceding step S6, but in particular step S5, are thus not part of the method according to the invention in these embodiments, but precede it, or the method according to the present invention is based on them.

Figure 7:
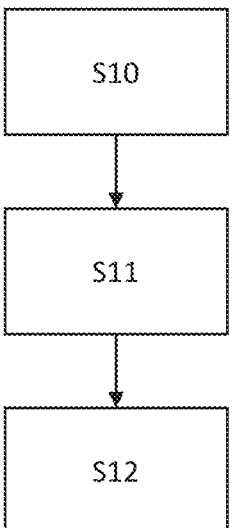
FIG. 7 shows a course of the method according to the invention for separating a tool from the machine tool in an exemplary embodiment.

FIG. 7 shows a course of the method according to the present invention for separating a tool 5 from a machine tool 4 in an exemplary embodiment.

Step S10 here represents the step of providing a machine tool 4, which has been prepared according to the method in FIG. 6 or to the alternative method described in FIG. 6, hence, is connected to a tool 5.

Step S11 represents moving the movable pins 19 projecting into the lumen 11 of the receptacle 1, for example against the effect of the spring, preferably until they flush with the stationary pins 17 in the lumen 11 of the receptacle 1.

Step S12 represents the withdrawal of the tool 5 from the machine tool 4 by pulling on the tool 5 and/or with the aid of gravity.

LIST OF REFERENCE NUMERALS

100 connection set
1 receptacle
11 lumen of receptacle
15 inner wall
17 stationary pin
19 movable pin
20 passage opening for movable pin
20a end of passage opening for movable pin
21 screw passage
23 passage for shaft coupling
24 inner section
25 outer section; rotating ring
25a circumferential groove
25b hole for torsion spring

26 torsion spring
27 finger section of rotating ring
3 insert
31 lumen of the insert
32 flange
33 sleeve section
35 guide
35a first section of the guide
35b second section of the guide
35c third section of the guide
39 end
4 machine tool
41 shaft coupling
5 attachment (here: drill chuck); tool
E1 first end of the torsion spring
E2 second end of the torsion spring
L longitudinal axis
L1 longitudinal axis
L2 longitudinal axis
α angle
K contact point between the movable pin and the side wall of the third section of the guide

The invention claimed is:

1. A connection set for connecting a tool to a hand-held machine tool, comprising:
a receptacle for being fastened to a machine tool and for receiving an insert;
an insert for attachment to a tool and for the releasable, at least sectionally, insertion into the receptacle,
wherein
the receptacle circumscribes a lumen of the receptacle which is continuous in the longitudinal direction of the receptacle, and the insert circumscribes a lumen of the insert which is continuous in the longitudinal direction of the insert;
the receptacle comprises at least one stationary pin which projects from an inner wall of the receptacle into the lumen of the receptacle and is stationary relative to the inner wall, and at least one movable pin which is movable relative to the inner wall and likewise projects into the lumen of the receptacle; and
the insert comprises on its outside at least one guide each of which is for guiding the at least one movable pin along the outside of the insert when the insert is being inserted into the lumen of the receptacle.

2. The connection set according to claim 1, wherein said at least one guide tapers from a first end of said insert towards a second end of said insert opposite to said first end in a first section of the at least one guide.

3. The connection set according to claim 2, wherein the first section of the at least one guide merges directly or indirectly into a second section of the at least one guide which does not taper.

4. The connection set according to claim 3, wherein the at least one guide comprises a third section which is at an angle of at least 15° to a longitudinal extension of the second section of the at least one guide.

5. The connection set according to claim 4, wherein the inner wall is part of an inner section of the receptacle, wherein the inner section of the receptacle comprises at least one passage opening through the inner wall for guiding the at least one movable pin at least also in a radial direction, and wherein the longitudinal axis (L2) of the at least one passage opening for the at least one movable pin is at an angle (α) to the longitudinal axis (L1) of the third section of the at least one guide in order to cause jamming of the at least one movable pin in the axial direction and/or in the circumferential direction.

6. The connection set according to claim 4, wherein an end of the third section of the at least one guide is closer to a flange of the insert that limits the depth of insertion of the insert into the receptacle in the axial direction than some or all other subsections of the third section of the at least one guide.

7. The connection set according to claim 1, wherein the inner wall is part of an inner section of the receptacle.

8. The connection set according to claim 1, having a device for moving the at least one movable pin.

9. The connection set according to claim 8, wherein the device for moving is, or comprises, an outer section of the receptacle or rotating ring of the receptacle which is provided to be rotatable relative to an inner section of the receptacle, the inner section comprising the inner wall.

10. The connection set according to claim 9, wherein the inner section of the receptacle comprises at least one passage opening through the inner wall for guiding the at least one movable pin at least also in a radial direction.

11. The connection set according to claim 10, wherein the at least one passage opening does not taper.

12. The connection set according to claim 1, wherein the receptacle comprises a fastening section for fastening the receptacle to the machine tool and a free end for receiving the insert, wherein at least one of the at least one stationary pin projecting into the lumen of the receptacle is arranged closer to the free end than at least one of the at least one movable pin.

13. The connection set according to claim 1, wherein the at least one guide of the insert, receiving the at least one movable pin and the at least one stationary pin of the receptacle, effects an axially and/or radially play-free reception of the insert in the receptacle.

14. The connection set according to claim 1, wherein a flange of the insert limits the depth of insertion of the insert into the receptacle in the axial direction.

15. The connection set according to claim 1, wherein the geometric configuration of the at least one guide of the insert causes the insert to be aligned independently with the receptacle when the insert is being inserted into the receptacle.

16. The connection set according to claim 1, wherein due to the interaction between the at least one guide of the insert with the at least one stationary pin and the at least one movable pin of the receptacle inserting the insert into the receptacle requires only the mere application of force, but otherwise no use of tools or no actuation or triggering of a mechanism, switch, or similar.

17. The connection set according to claim 1, wherein the at least one movable pin is, directly or indirectly, biased or loaded by a spring.

18. The connection set according to claim 17, having a device for moving the at least one movable pin, against the effect of the spring by which the at least one movable pin is directly or indirectly, biased or loaded.

19. The connection set according to claim 1, wherein the at least one guide comprises a section which is at an angle of at least 15° to a longitudinal axis (L) of the insert.

20. A set, comprising or consisting of a hand-held machine tool, at least one tool and/or at least one connection set according to claim 1.

21. A method for separating a tool from a machine tool, encompassing the steps of providing a machine tool connected to a tool in accordance with a method of providing a hand-held machine tool;

providing a tool for the machine tool;

providing a connection set according to claim 1;

connecting the receptacle of the connection set to the machine tool;

connecting the insert of the connection set to the tool; and connecting the insert to the receptacle by inserting the insert, at least in sections, into the lumen of the receptacle;

moving the movable pins projecting into the lumen of the receptacle, in particular against the effect of the optional spring;

withdrawing the tool from the machine tool by pulling on the tool and/or with the aid of gravity.

\* \* \* \* \*